(12) United States Patent
Miura et al.

(10) Patent No.: US 8,049,179 B2
(45) Date of Patent: Nov. 1, 2011

(54) ULTRAVIOLET RADIATION DETECTOR AND APPARATUS FOR EVALUATING ULTRAVIOLET RADIATION PROTECTION EFFECT

(75) Inventors: Yoshimasa Miura, Yokohama (JP); Yoshihiro Takiguchi, Hamamatsu (JP); Masayuki Shirao, Yokohama (JP); Sadaki Takata, Yokohama (JP); Masato Hatao, Yokohama (JP); Hiroshi Fukui, Tokyo (JP)

(73) Assignees: Shiseido Company, Ltd., Tokyo (JP); Hamamatsu Photonics K.K., Shizuoka (JP)

( * ) Notice: Subject to any disclaimer, the term of this patent is extended or adjusted under 35 U.S.C. 154(b) by 331 days.

(21) Appl. No.: 12/443,829

(22) PCT Filed: Oct. 3, 2007

(86) PCT No.: PCT/JP2007/069372
§ 371 (c)(1),
(2), (4) Date: Apr. 1, 2009

(87) PCT Pub. No.: WO2008/044576
PCT Pub. Date: Apr. 17, 2008

(65) Prior Publication Data
US 2010/0012850 A1 Jan. 21, 2010

(30) Foreign Application Priority Data
Oct. 6, 2006 (JP) .................................. 2006-275374

(51) Int. Cl.
*G01J 1/02* (2006.01)

(52) U.S. Cl. ...................................................... 250/372
(58) Field of Classification Search .................. 250/372, 250/373
See application file for complete search history.

(56) References Cited

U.S. PATENT DOCUMENTS
2004/0200975 A1 * 10/2004 Brown et al. ................. 250/372

FOREIGN PATENT DOCUMENTS

| | | |
|---|---|---|
| JP | 05-075157 | 3/1993 |
| JP | 07-167781 | 7/1995 |
| JP | 2001-242075 | 9/2001 |
| JP | 2001242075 A * | 9/2001 |
| JP | 2004-311171 | 11/2004 |
| WO | WO 99/01745 | 1/1999 |

OTHER PUBLICATIONS

Minoru Fukuda et al., "Studies on several factors affecting SPF", Journal of SCCJ, Dec. 15, 1985, vol. 19, No. 1, pp. 38 to 47.
Nature, May 10, 2007, vol. 447, No. 7141, p. 150.

* cited by examiner

*Primary Examiner* — Mark R Gaworecki
(74) *Attorney, Agent, or Firm* — IPUSA, PLLC

(57) ABSTRACT

An ultraviolet radiation detector 10, detecting an ultraviolet radiation transmitted through or reflected from a measurement sample 15 from a light beam including at least the ultraviolet radiation, is characterized by spectral means 19 for spectrally splitting the ultraviolet radiation from the light beam and photodetection means 20 for detecting the ultraviolet radiation spectrally split by the spectral means 19, the photodetection means 20 including a photoelectric surface detecting only the ultraviolet radiation and formed of an element selected from In, Ga, N, Al, O and Cs.

13 Claims, 6 Drawing Sheets

ULTRAVIOLET RADIATION DETECTOR AND APPARATUS FOR EVALUATING ULTRAVIOLET RADIATION PROTECTION EFFECT

TECHNICAL FIELD

The present invention relates to an ultraviolet radiation detector and an apparatus for evaluating an ultraviolet radiation protection effect.

BACKGROUND ART

Erythema and tanning as human body reactions to ultraviolet radiation tend to be considered as phenomena caused by exposure to ultraviolet radiation only. However, it is considered that more complicated immune phenomena are actually caused by simultaneous exposure to visible radiation and infrared radiation as well as ultraviolet radiation. In this sense, an apparatus is necessary that can detect only ultraviolet radiation with high sensitivity under exposure to light including visible radiation and infrared radiation as well as ultraviolet radiation in developing sun protection products for protecting human bodies from ultraviolet radiation.

Conventionally, however, no ultraviolet radiation detector has been available as a product that separates and evaluates only the effect of ultraviolet radiation under exposure to visible radiation and infrared radiation as well. Therefore, conventional ultraviolet radiation detectors adopt the method of eliminating the effect of visible radiation in detection by attenuating visible radiation by subjecting a light beam emitted from a white light such as a xenon lamp to an ultraviolet radiation transmission filter, exposing a measurement sample to the light beam with the attenuated visible radiation, and spectrally splitting the light beam reflected from or passing through the measurement sample using a spectrometer.

For example, there is an apparatus that calculates the in vitro predicted SPF, frequently used as an index of the ultraviolet radiation protection effect, by measuring the intensity of ultraviolet radiation that has passed through a sun protection product. (See, for example, Patent Document 1). However, the conventional apparatus fails to detect faint ultraviolet radiation with good sensitivity because of its low ultraviolet radiation detectivity due to poor wavelength resolution or low detectivity resulting from a low signal amplification factor.

Further, such ultraviolet radiation detectors as described above employ photodetectors also sensitive to light beams other than ultraviolet radiation, such as silicon photodiode detectors, photomultipliers, and CCD cameras. Therefore, attempts have been made to extract only ultraviolet radiation using various combinations of ultraviolet radiation transmission filters in order to evaluate only the effect of ultraviolet radiation.

[Patent Document 1] U.S. Pat. No. 3,337,832

DISCLOSURE OF THE INVENTION

Problem(s) to be Solved by the Invention

However, there is a problem in that only a few of such ultraviolet radiation transmission filters that transmit only an ultraviolet radiation range and do not transmit light of wavelengths other than ultraviolet radiation as described above are practicable in a strict sense.

Further, exposure to ultraviolet radiation causes a measurement sample and materials therearound to generate fluorescence or phosphorescence. Therefore, there is a problem in that the conventional photodetector also sensitive to light beams other than ultraviolet radiation may include scattered components of this fluorescence or phosphorescence in measurements.

The present invention is made in view of the above-described points, and has an object of providing an ultraviolet radiation detector and an apparatus for evaluating an ultraviolet radiation protection effect that can detect only ultraviolet radiation with high sensitivity.

The present invention is characterized by taking the following measures in order to achieve the above-described object.

An ultraviolet radiation detector of the present invention, detecting an ultraviolet radiation transmitted through or reflected from a measurement sample from a light beam including at least the ultraviolet radiation, includes spectral means for spectrally splitting the ultraviolet radiation from the light beam and photodetection means for detecting the ultraviolet radiation spectrally split by the spectral means, the photodetection means including a photoelectric surface detecting only the ultraviolet radiation and formed of an element selected from In, Ga, N, Al, O and Cs.

An apparatus for evaluating an ultraviolet radiation protection effect of the present invention calculates the in vitro predicted SPF and the in vivo SPF of a measurement sample by using the ultraviolet radiation detector.

Effect(s) of the Invention

According to the present invention, it is possible to detect only ultraviolet radiation with high sensitivity.

Figure 1:
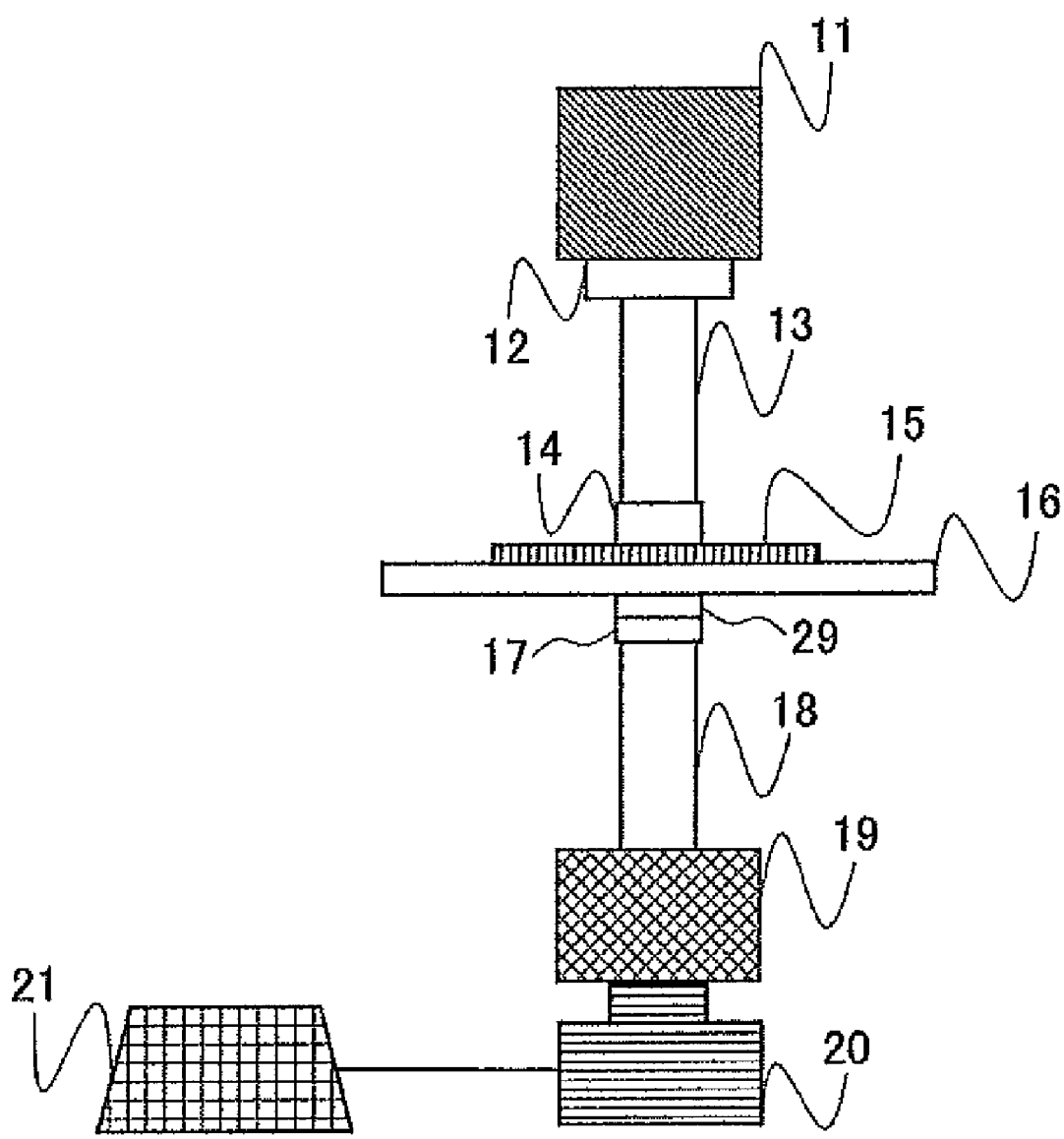
FIG. 1 is a configurational diagram of an ultraviolet radiation detector in a first embodiment of the present invention.

| DESCRIPTION OF THE REFERENCE NUMERALS | |
|---|---|
| 10, 30, 50 | Ultraviolet radiation detector |
| 11, 31, 51 | Light source |
| 12, 52 | Filter |
| 13, 33, 53 | First optical fiber |
| 14, 34, 54 | Irradiation port |
| 15, 55 | Measurement sample |
| 16, 56 | Measurement sample substrate |
| 17, 37, 57 | Detection port |
| 18, 38, 58 | Second optical fiber |
| 19, 39, 59 | Spectrometer |
| 20, 40, 60 | Photodetector |
| 21, 41, 61 | Computer |
| 29, 49, 69 | Integrating sphere |
| 32 | First filter |
| 35 | Measurement sample and/or measurement living body |
| 42 | Second filter |

-continued

DESCRIPTION OF THE REFERENCE NUMERALS

| 43 | Intermittent exposure shutter |
|---|---|
| 62 | Lock-in amplifier |
| 63 | Light chopper |

BEST MODE(S) FOR CARRYING OUT THE INVENTION

Next, the best modes for carrying out the present invention are described as embodiments with reference to the drawings.

First Embodiment

FIG. 1 is a configurational diagram of an ultraviolet radiation detector in a first embodiment of the present invention.

Referring to FIG. 1, an ultraviolet radiation detector 10, which is an apparatus in the case of having a measurement sample 15 as a sample, includes a light source 11, a filter 12, a first optical fiber 13, an irradiation port 14, a measurement sample substrate 16, an integrating sphere 29, a detection port 17, a second optical fiber 18, a spectrometer 19, a photodetector 20, and an electrical signal processor and analyzer (computer 21).

The light source 11, for which a xenon lamp, which is a white light including ultraviolet radiation, visible radiation, and infrared radiation, is suitably used in the first embodiment, is not limited to this. Further, the xenon lamp, which is a white light source, can be used as simulated sunlight.

The filter 12, which is in the vicinity of the light source 11 in a direction in which light travels from the light source 11, is a filter that corrects the ultraviolet radiation spectrum of a light beam emitted from the light source 11.

Figure 2:
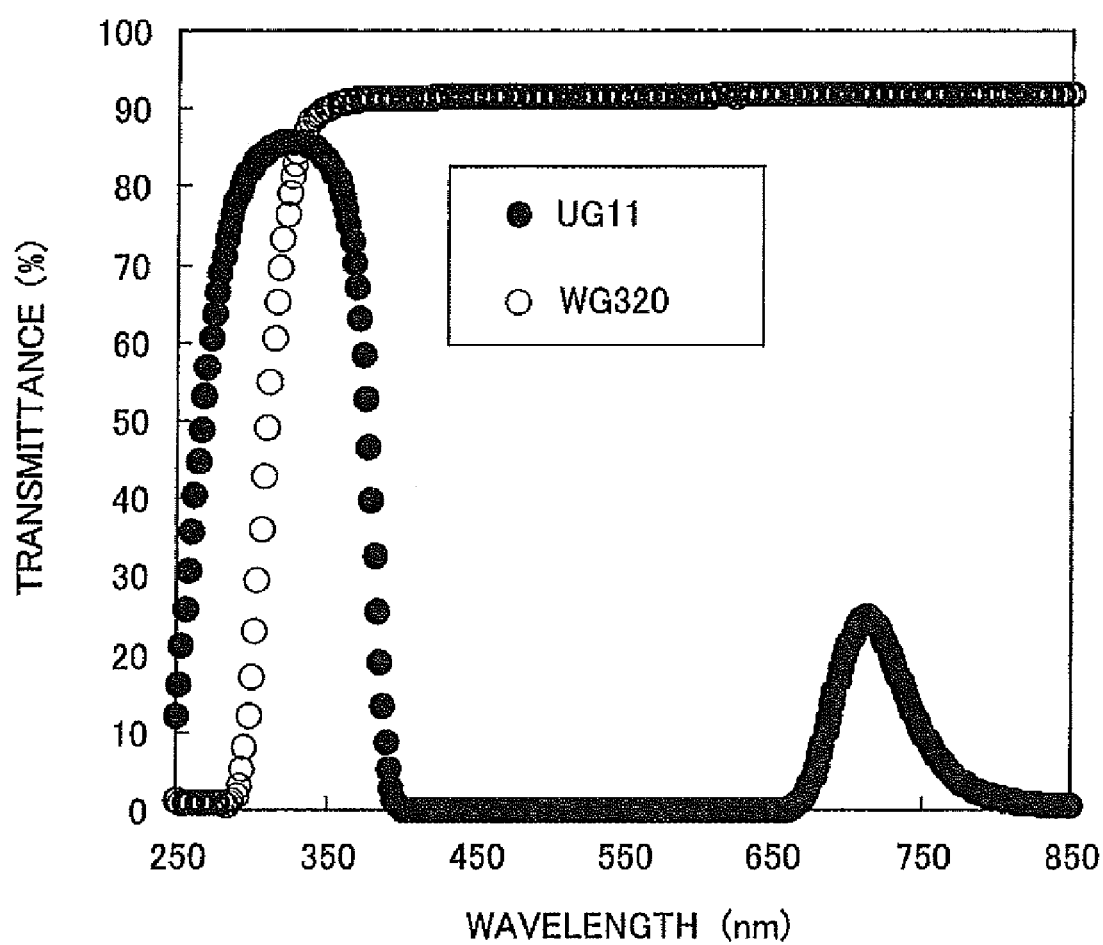
FIG. 2 is a characteristic diagram of a filter of the first embodiment.

FIG. 2 is a characteristic diagram of the filter of the first embodiment.

Referring to FIG. 2, the horizontal axis represents wavelength (nm) and the vertical axis represents transmittance (%). The conventional filter, for example, a UG11 manufactured by SCHOTT AG, has the wavelength characteristic of extracting only ultraviolet radiation as indicated by black circles in the drawing. On the other hand, the filter 12 of the first embodiment, for example, a WG320 manufactured by SCHOTT AG, is characterized by being a filter that transmits light beams of longer wavelength than ultraviolet radiation as indicated by white circles in the drawing.

The conventional filter is obtained by mixing various materials into a glass base material so as to present the wavelength characteristic as indicated by the black circles of the drawing, while the filter of the first embodiment is formed simply of transparent glass with a controlled composition. Therefore, it is possible to reduce the manufacturing cost of the entire ultraviolet radiation detector 10 by using the filter 12 of the first embodiment.

Referring back to FIG. 1, the first optical fiber 13 is in the vicinity of the filter 12 in a direction in which light travels from the filter 12. The first optical fiber 13 guides a light beam that has passed through the filter 12 to the irradiation port 14.

The light beam is emitted from the irradiation port 14. The irradiation port 14 and the detection port 17 are fixed at a predetermined interval, and the measurement sample substrate 16, on which the measurement sample 15 is placed, is fixed at a certain distance from the irradiation port 14. The irradiation port 14, the measurement sample 15, the measurement sample substrate 16, and the integrating sphere 29 are arranged in this order when indicated in order of light traveling.

The measurement sample substrate 16, which is a sample support on which the measurement sample is placed, is preferably formed of a material that does not absorb ultraviolet radiation.

The integrating sphere 29 receives a light beam that has passed through the measurement sample 15 and the measurement sample substrate 16, concentrates the light beam, and makes the light beam uniform by spatially integrating the light beam. The integrating sphere 29 may be omitted.

The detection port 17 receives the light beam made uniform by the integrating sphere 29, and guides the light beam to the second optical fiber 18 described below.

The second optical fiber 18 is in the vicinity of the detection port 17 in a direction in which light travels from the detection port 17. The second optical fiber 18 guides the light beam received by the detection port 17 to the spectrometer 19.

The spectrometer 19 is a light splitting means for spectrally splitting the light beam from the second optical fiber 18 at intervals of 1 nm in a 290 nm to 400 nm range, which is an ultraviolet radiation range. The photodetector 20 described below is exposed to the ultraviolet radiation spectrally split by the spectrometer 19.

The spectrometer 19 of the first embodiment, which has its sensitivity characteristic adjusted to ultraviolet radiation, realizes a highly sensitive spectral performance by using a diffraction grating having a good sensitivity characteristic in an ultraviolet radiation range of 200 nm to 400 nm in particular. Specifically, a concave diffraction grating (model number 10-015) manufactured by Shimadzu Corporation or the like is selected, but the spectrometer 19 is not limited to this.

Figure 3:
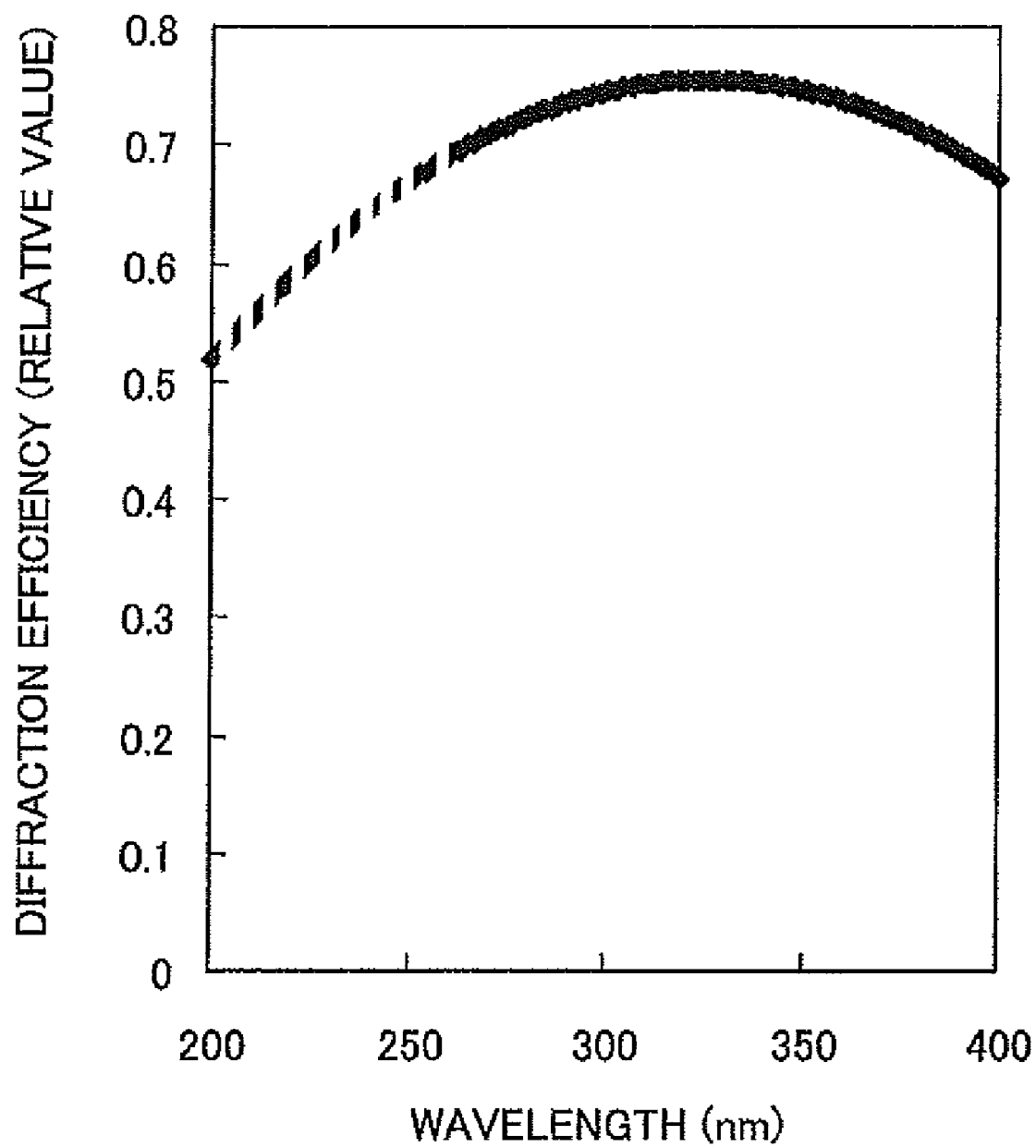
FIG. 3 is a characteristic diagram of the sensitivity of the diffraction grating of a spectrometer in the first embodiment.

FIG. 3 is a characteristic diagram of the sensitivity of the diffraction grating of the spectrometer in the first embodiment.

Referring to FIG. 3, the horizontal axis represents wavelength (nm) and the vertical axis represents diffraction efficiency (relative value).

The sensitivity characteristic of the concave diffraction grating that is the spectrometer 19 of the first embodiment has high sensitivity to an ultraviolet radiation range of 200 nm to 400 nm, and in particular, the diffraction efficiency (relative value) in the 200 nm to 400 nm range is more than or equal to 0.5. This characteristic shows high suitability for use as the diffraction grating of the spectrometer 19 of the first embodiment.

The photodetector 20 detects the ultraviolet radiation split by the spectrometer 19 with an optical sensor, and converts the intensity of a light beam of each wavelength into a current or voltage signal. This current or voltage signal is transmitted to the computer 21 connected to the photodetector 20 with an electrical interconnection.

With recent progress in faint light detection techniques, photomultipliers with enhanced detection sensitivity are often used. It is apparent also theoretically that photomultipliers have higher detection sensitivity than conventional photodiode arrays and CCDS, but it is necessary to select the material of the photoelectric surface of the photomultiplier depending on the wavelength region of light to be detected.

The photodetector 20 serving as the photodetection means of the first embodiment realizes a highly sensitive ultraviolet radiation detector by employing a photomultiplier having a good sensitivity characteristic in an ultraviolet radiation range of 200 nm to 400 nm in particular. Specifically, a photomultiplier is used that has a photoelectric surface formed of materials selected from elements such as In, Ga, N, Al, O, and Cs.

Figure 4:
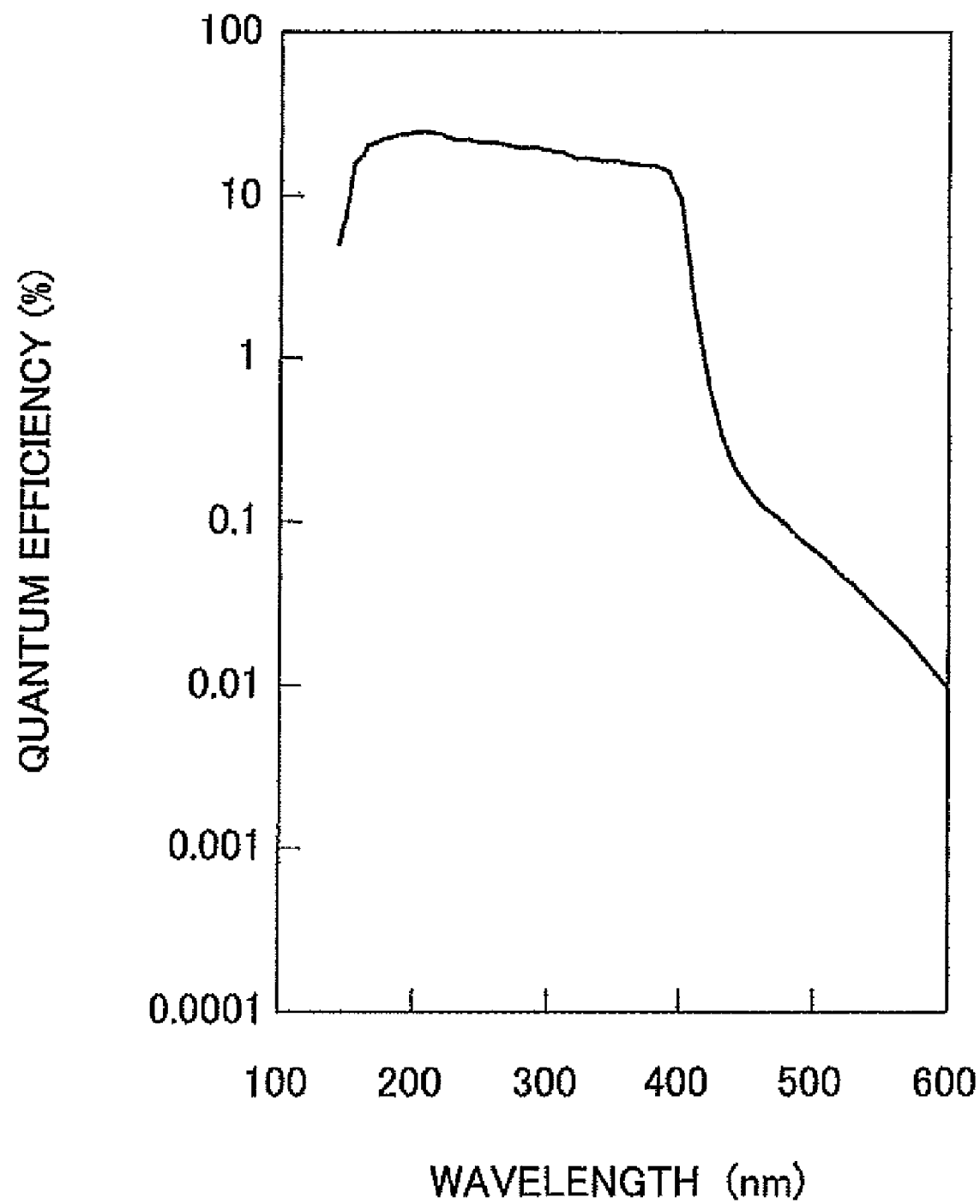
FIG. 4 is a characteristic diagram of the spectral sensitivity of an InGaN photoelectric surface of the first embodiment.

FIG. 4 is a characteristic diagram of the spectral sensitivity of an InGaN photoelectric surface of the first embodiment.

Referring to FIG. 4, the horizontal axis represents wavelength (nm) and the vertical axis represents quantum efficiency (%). The spectral sensitivity of the InGaN photoelectric surface of the photomultiplier that is the photodetector 20 of the first embodiment has high sensitivity to an ultraviolet radiation range of 160 nm to 400 nm, and in particular, the quantum efficiency in a 200 nm to 400 nm range is more than or equal to 0.1. Further, the quantum efficiency shows higher sensitivity to the ultraviolet radiation range than to light beams of wavelengths longer than or equal to 400 nm by two to three digits. This characteristic shows high suitability for use as the photodetector 20 of the ultraviolet radiation detector 10 of the first embodiment.

A description is given above of the case of using a photomultiplier for the photodetector 20. However, it is also possible to use a semiconductor photodetector formed of In, Ga, N, Al, O, etc., as the photodetector 20 in the same manner.

Referring back to FIG. 1, the computer 21 receives data from the photodetector 20 and processes the data into a format easily understandable by a user, so that the results can be displayed on a screen, printed out on recording paper, or stored in a storage medium.

Conventionally, the above-described optical system from the light source 11 to the photodetector 20 includes expensive materials using such quartz-based materials that are not caused to generate fluorescence or phosphorescence by ultraviolet radiation as described above. However, in the first embodiment, the detector has sensitivity only to the ultraviolet radiation range. Therefore, even if materials generate fluorescence or phosphorescence in the visible radiation range, its effect does not appear in signal output. Therefore, the optical system can be formed of inexpensive optical materials, so that it is possible to reduce the manufacturing cost of the entire ultraviolet radiation detector 10.

According to the first embodiment, it is possible to evaluate the effect of ultraviolet radiation on a sample under visible radiation by using a photodetector having sensitivity only to ultraviolet radiation.

Further, it is possible to make an apparatus structure for pursuing the possibility of intensifying a phenomenon induced by ultraviolet radiation in a measurement sample by visible radiation.

Further, as an optical device used for configuring an apparatus, it is less likely to affect measurements even with fluorescence or phosphorescence caused by ultraviolet radiation excitation as described above. Accordingly, it is also possible to make an inexpensive apparatus configuration.

Second Embodiment

Figure 5:
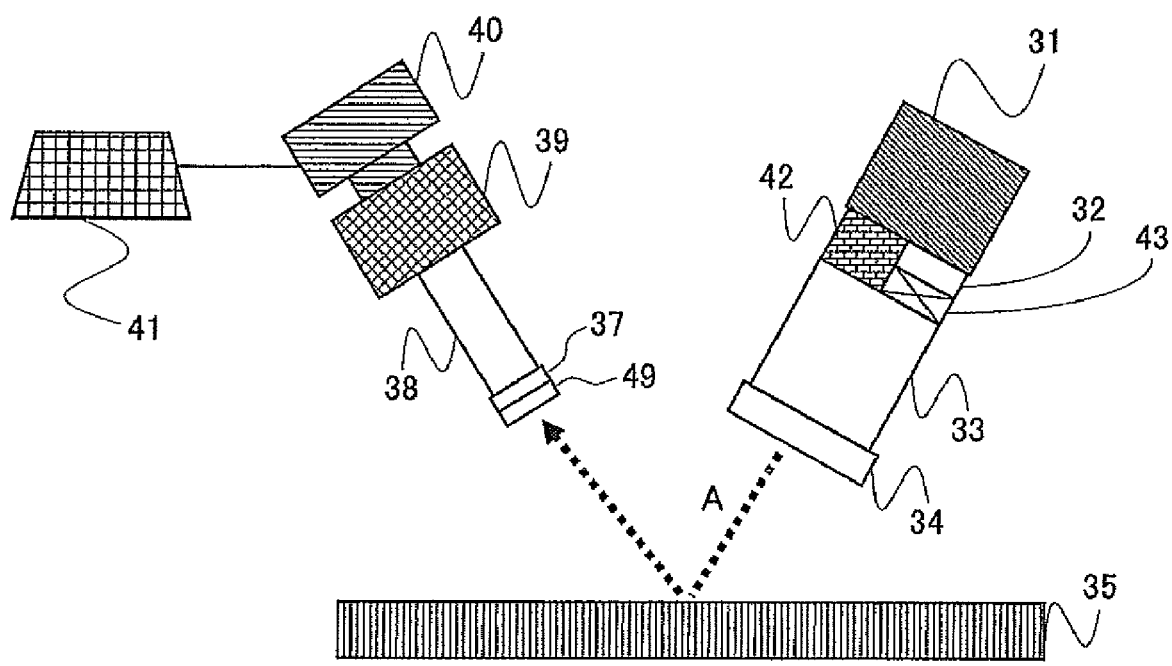
FIG. 5 is a configurational diagram of an ultraviolet radiation detector in a second embodiment of the present invention.

FIG. 5 is a configurational diagram of an ultraviolet radiation detector in a second embodiment of the present invention.

Referring to FIG. 5, an ultraviolet radiation detector 30, which is an apparatus in the case of having a measurement sample 35 as a sample, includes a light source 31, a first filter 32, a second filter 42, an intermittent exposure shutter 43, a first optical fiber 33, an irradiation port 34, an integrating sphere 49, a detection port 37, a second optical fiber 38, a spectrometer 39, a photodetector 40, and an electrical signal processor and analyzer (computer 41).

The ultraviolet radiation detector 30 is an apparatus for evaluating the ultraviolet radiation reflection properties of the measurement sample 35 including a biological sample by emitting visible radiation intermittently or continuously while emitting ultraviolet radiation constantly. While the ultraviolet radiation detector 10 of the first embodiment is an apparatus for detecting a test light beam that has passed through the measurement sample 15, the ultraviolet radiation measurement apparatus 30 is an apparatus for detecting a test light beam reflected from the surface of the measurement sample 35. In view of this characteristic, the ultraviolet radiation detection apparatus 30 is an apparatus suitable for using an actual living body as the measurement sample.

The light source 31 has the same configuration as the light source 11 of the first embodiment. However, a light beam is emitted from the light source 31 onto the below-described first filter 32 and second filter 42.

The first filter 32, which is in the vicinity of the light source 31 in a direction in which light travels from the light source 31, is a filter that corrects the ultraviolet radiation spectrum of the light beam emitted from the light source 31. Since the first filter 32 has the same configuration as the filter 12 of the first embodiment, a detailed description thereof is omitted. The light beam that has passed through the first filter 32 is emitted onto the below-described intermittent exposure shutter 43.

The intermittent exposure shutter 43 is a shutter that intermittently shuts out the light beam that has passed through the first filter 32. It is also possible to have the shutter open constantly for continuous passage of the light beam. The light beam that has passed through the intermittent exposure shutter 43 is emitted to the first optical fiber 33.

The second filter 42, which is in the vicinity of the light source 31 in a direction in which light travels from the light source 31, turns the light beam emitted from the light source 31 into UVB and UVA ultraviolet radiation of 290 nm to 400 nm wavelengths. The second filter 42, for which a WG320 filter and a UG11 filter (both manufactured by SCHOTT AG) are suitably used, is not limited to these. The light beam that has passed through the second filter 42 is emitted to the first optical fiber 33.

The first optical fiber 33, which is in the vicinity of the first filter 32 and the second filter 42 in a direction in which light travels from the first filter 32 and the second filter 42, guides the light beams that have passed through the first filter 32 and the second filter 42 to the irradiation port 34.

Describing the configuration up to here, ultraviolet radiation, visible radiation, and infrared radiation are emitted from the irradiation port 34 with the intermittent exposure shutter 43 being open. On the other hand, with the intermittent exposure shutter 43 being closed intermittently, ultraviolet radiation is emitted constantly while visible radiation and infrared radiation are emitted intermittently only when the intermittent exposure shutter 43 is open.

The above-described light beam is emitted from the irradiation port 34 onto the measurement sample 35. The light beam emitted onto the measurement sample 35 is indicated by A in the drawing. The light beam A emitted from the irradiation port 34 reaches the surface of the measurement sample 35 to be absorbed or transmitted by the measurement sample 35 with a portion of the light beam A being reflected from the surface of the measurement sample 35. This reflected portion of the light beam is received by the integrating sphere 49.

The integrating sphere 49, the detection port 37, the second optical fiber 38, the spectrometer 39, the photodetector 40, and the computer 41 have the same configurations as the integrating sphere 29, the detection port 17, the second optical fiber 18, the spectrometer 19, the photodetector 20, and the computer 21, respectively, of the first embodiment, and accordingly, a detailed description thereof is omitted.

According to the second embodiment, in addition to the effects of the first embodiment, it is possible to measure the skin of a living body and the surface of an unbreakable object because the ultraviolet radiation detector detects reflected light from the surface of a sample measurement.

Further, the workings of the intermittent exposure shutter make it possible to control the presence or absence of emission of visible radiation and infrared radiation separately from emission of ultraviolet radiation to a measurement sample. Therefore, it is possible to compare an evaluation at the time of emission of ultraviolet radiation and an evaluation at the time of emission of ultraviolet radiation, visible radiation, and infrared radiation with respect to the measurement sample.

Third Embodiment

Figure 6:
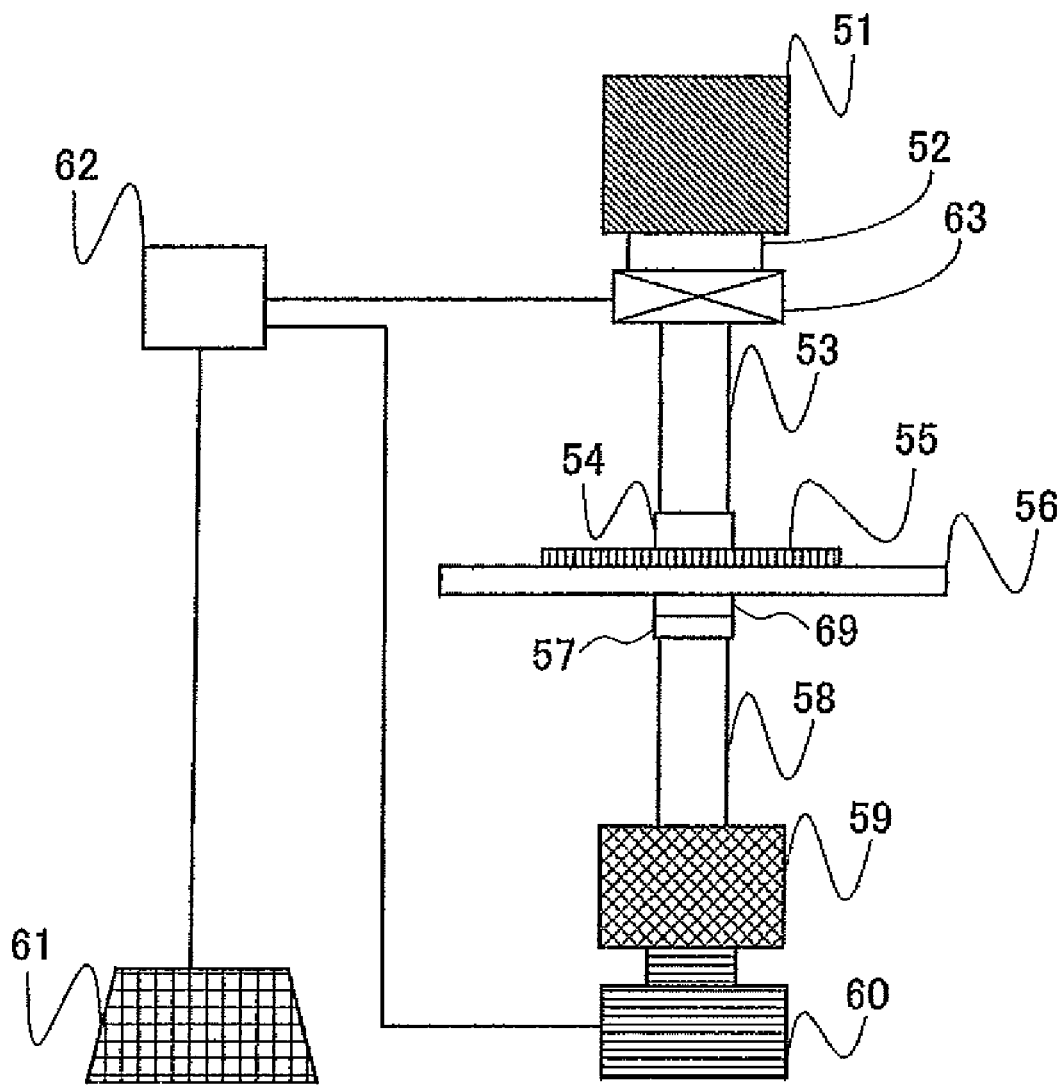
FIG. 6 is a configurational diagram of an ultraviolet radiation detector in a third embodiment of the present invention.

FIG. 6 is a configurational diagram of an ultraviolet radiation detector in a third embodiment of the present invention.

Referring to FIG. 6, an ultraviolet radiation detector 50, which is an apparatus in the case of having a measurement sample 55 as a sample, includes a light source 51, a filter 52, a light chopper 63, a first optical fiber 53, an irradiation port 54, a measurement sample substrate 56, an integrating sphere 69, a detection port 57, a second optical fiber 58, a spectrometer 59, a photodetector 60, an electrical signal processor and analyzer (computer 61), and a lock-in amplifier 62.

Since the light source 51 has the same configuration as the light source 11 of the first embodiment, a detailed description thereof is omitted.

Likewise, since the filter 52 has the same configuration as the filter 12 of the first embodiment, a detailed description thereof is omitted. However, a light beam that has passed through the filter 52 is emitted to the light chopper 63.

The light chopper 63, which is a shutter that intermittently transmits the light beam that has passed through the filter 52, emits the light beam in pulses. This light beam is emitted in pulses to the first optical fiber 53.

Further, the light chopper 63 is electrically connected to the below-described lock-in amplifier 62, so that the pulsed light and a synchronization signal are obtained from the drive circuit 62, thereby performing synchronization analysis on a signal from the below-described photodetector 60.

The first optical fiber 53, the irradiation port 54, the measurement sample substrate 56, the integrating sphere 69, the detection port 57, the second optical fiber 58, the spectrometer 59, the photodetector 60, and the computer 61 have the same configurations as the first optical fiber 13, the irradiation port 14, the measurement sample substrate 16, the integrating sphere 29, the detection port 17, the second optical fiber 18, the spectrometer 19, the photodetector 20, and the computer 21, and accordingly, a detailed description thereof is omitted.

However, the computer 61 is electrically connected to the lock-in amplifier 62, and receives a numerical value after detection of a signal from the photodetector 60 in the lock-in amplifier 62.

The lock-in amplifier 62 is electrically connected to the photodetector 60, the computer 61, and the light chopper 63. The lock-in amplifier 62 performs control so as to synchronize the pulsed light emitted from the light chopper 63 and a signal received from the photodetector 60. Specifically, this synchronization control synchronizes the two signals using a phase detector circuit in the lock-in amplifier 62.

According to the third embodiment, in addition to the effects of the first embodiment, it is possible to evaluate properties of the measurement sample 55, which is degraded fast by ultraviolet radiation included in a test light beam, at high speed with instantaneous irradiation of a light beam by the above-described control. This method makes it possible to complete measurement before degradation of the measurement sample 55.

Further, a phenomenon caused in a measurement sample by a pulsed light beam (such as the photodegradation of the measurement sample caused by ultraviolet radiation) is relaxed by arbitrarily changing the time width of a pulse emission and pulse emission intervals without changing the total time of emission of a light beam onto the measurement sample. It is also possible to evaluate the relaxation process of such a sample that becomes less affected by ultraviolet radiation between a pulse emission and reception of the next pulse emission.

Fourth Embodiment

As a fourth embodiment, the ultraviolet radiation detector 10 of the first embodiment and the ultraviolet radiation detector 50 of the third embodiment are used as methods of evaluating an ultraviolet radiation protection effect in the above-described sun protection product. Specifically, the in vitro predicted SPF of the sun protection product is calculated.

In the ultraviolet radiation detectors 10 and 50 of the first and third embodiments, the in vitro predicted SPF can be calculated by applying the sun protection product on the measurement sample substrates 16 and 56, which are skin substitute films, as the measurement samples 15 and 55, exposing the measurement samples 15 and 55 to test light, detecting the test light transmitted through the measurement samples 15 and 55 with the photodetectors 20 and 60, and analyzing the spectrum of this transmitted light. Specifically, the method disclosed in Patent Document 1 can be employed in the ultraviolet radiation detectors 10 and 50 of the first and third embodiments.

Further, the ultraviolet radiation detectors 10 and 50 have extremely high ultraviolet radiation detectivity as described above. Therefore, the ultraviolet radiation detectors 10 and 50 can ensure detection of even weak ultraviolet radiation in the light transmitted through a measurement sample showing a high SPF.

Fifth Embodiment

As a fifth embodiment, the ultraviolet radiation detector 30 of the second embodiment is used as a method of evaluating an ultraviolet radiation protection effect in the above-described sun protection product. Specifically, the in vitro predicted SPF of the sun protection product is calculated.

In the ultraviolet radiation detector 30 of the second embodiment, the in vitro predicted SPF can be calculated by applying the sun protection product on the measurement living body 35 as a measurement sample, exposing the measurement living body 35 to test light, detecting the test light reflected from the measurement sample with the photodetector 40, and analyzing the spectrum of this reflected light.

A detailed description is given above of preferred embodiments of the present invention. However, the present invention is not limited to these specific embodiments, and variations and modifications can be made within the gist of the present invention described in CLAIMS. Interchanges in arrangement in the apparatus configuration, for example, the arrangement of a spectrometer and a light chopper, are not limited to the embodiments.

Further, these apparatuses, which may be used in a 290 nm to 400 nm range in the case of evaluating the ultraviolet radiation protection effect of a sun protection product, can be applied broadly in a 200 nm to 400 nm range.

The present international application claims priority based on Japanese Patent Application No. 2006-275374, filed on Oct. 6, 2006, the entire contents of which are incorporated in the present international application.

The invention claimed is:

1. An ultraviolet radiation detector detecting an ultraviolet radiation transmitted through or reflected from a measurement sample from a light beam including at least the ultraviolet radiation, comprising:
   a spectral part configured to spectrally split the ultraviolet radiation from the light beam; and
   a photodetection part configured to detect the ultraviolet radiation spectrally split by the spectral part, to convert a light beam intensity of each of wavelengths of the spectrally-split ultraviolet radiation into one of a current signal and a voltage signal, and to output the one of the current signal and the voltage signal to an external computer, the photodetection part including a photoelectric surface detecting only the ultraviolet radiation and formed of an element selected from in, Ga, N, Al, O and Cs.

2. The ultraviolet radiation detector as claimed in claim 1, wherein the photodetection part uses a photomultiplier having a sensitivity characteristic adjusted to the ultraviolet radiation.

3. The ultraviolet radiation detector as claimed in claim 2, wherein the photomultiplier has a quantum efficiency of 0.1 or more in a 200 nm to 400 nm wavelength range.

4. The ultraviolet radiation detector as claimed in claim 1, wherein the spectral part has a sensitivity characteristic adjusted to the ultraviolet radiation and has a wavelength resolution of 1 nm or less.

5. The ultraviolet radiation detector as claimed in claim 4, wherein the spectral part has a diffraction grating having a diffraction efficiency of 0.5 in relative value or more in a 200 nm to 400 nm wavelength range.

6. The ultraviolet radiation detector as claimed in claim 1, wherein the light beam is emitted onto the measurement sample and the ultraviolet radiation reflected from the measurement sample is detected.

7. The ultraviolet radiation detector as claimed in claim 1, wherein a xenon lamp is used as a light source emitting the light beam.

8. The ultraviolet radiation detector as claimed in claim 7, wherein the xenon lamp is used as simulated sunlight.

9. An ultraviolet radiation detector detecting an ultraviolet radiation transmitted through or reflected from a measurement sample from a light beam including at least the ultraviolet radiation, comprising:
   a spectral part configured to spectrally split the ultraviolet radiation from the light beam; and
   a photodetection part configured to detect the ultraviolet radiation spectrally split by the spectral part, the photodetection part including a photoelectric surface detecting only the ultraviolet radiation and formed of an element selected from In, Ga, N, Al, O and Cs,
   wherein the light beam is emitted onto the measurement sample and the ultraviolet radiation transmitted through the measurement sample is detected.

10. An ultraviolet radiation detector detecting an ultraviolet radiation transmitted through or reflected from a measurement sample from a light beam including at least the ultraviolet radiation, further comprising:
    a spectral part configured to spectrally split the ultraviolet radiation from the light beam;
    a photodetection part configured to detect the ultraviolet radiation spectrally split by the spectral part, the photodetection part including a photoelectric surface detecting only the ultraviolet radiation and formed of an element selected from In, Ga, N, Al, O and Cs;
    a light chopper configured to emit the light beam onto the measurement sample in pulses; and
    a lock-in amplifier configured to synchronize signals of the light chopper and the photodetection part.

11. An ultraviolet radiation detector detecting an ultraviolet radiation transmitted through or reflected from a measurement sample from a light beam including at least the ultraviolet radiation, comprising:
    a spectral part configured to spectrally split the ultraviolet radiation from the light beam; and
    a photodetection part configured to detect the ultraviolet radiation spectrally split by the spectral part, the photodetection part including a photoelectric surface detecting only the ultraviolet radiation and formed of an element selected from In, Ga, N, Al, O and Cs,
    wherein a time width and an interval of an emission of the light beam is changeable without changing a total time of the emission of the light beam onto the measurement sample where an ultraviolet radiation transmission characteristic of the measurement sample changes due to exposure to the light beam.

12. An ultraviolet radiation detector detecting an ultraviolet radiation transmitted through or reflected from a measurement sample from a light beam including at least the ultraviolet radiation, comprising:
    a spectral part configured to spectrally split the ultraviolet radiation from the light beam; and
    a photodetection part configured to detect the ultraviolet radiation spectrally split by the spectral part, the photodetection part including a photoelectric surface detecting only the ultraviolet radiation and formed of an element selected from In, Ga, N, Al, O and Cs,
    wherein the ultraviolet radiation is emitted continuously onto the measurement sample and visible radiation is emitted continuously or intermittently onto the measurement sample.

13. An apparatus for evaluating an ultraviolet radiation protection effect, wherein by using an ultraviolet radiation detector detecting an ultraviolet radiation transmitted through or reflected from a measurement sample from a light beam including at least the ultraviolet radiation, an in vitro predicted SPF and an in vivo SPF of the measurement sample are calculated, the ultraviolet radiation detector including a spectral part configured to spectrally split the ultraviolet radiation from the light beam, and a photodetection part configured to detect the ultraviolet radiation spectrally split by the spectral part, the photodetection part including a photoelectric surface detecting only the ultraviolet radiation and formed of an element selected from In, Ga, N, Al O and Cs.

* * * * *